United States Patent
Hein et al.

(10) Patent No.: US 6,904,117 B2
(45) Date of Patent: Jun. 7, 2005

(54) TILTED GANTRY HELICAL CONE-BEAM FELDKAMP RECONSTRUCTION FOR MULTISLICE CT

(75) Inventors: Ilmar Arthur Hein, Schaumburg, IL (US); Katsuyuki Taguchi, Buffalo Grove, IL (US)

(73) Assignee: Toshiba Corporation, Tokyo (JP)

( * ) Notice: Subject to any disclaimer, the term of this patent is extended or adjusted under 35 U.S.C. 154(b) by 19 days.

(21) Appl. No.: 10/283,080

(22) Filed: Oct. 30, 2002

(65) Prior Publication Data

US 2004/0086075 A1 May 6, 2004

(51) Int. Cl.[7] .............................................. A61B 6/00
(52) U.S. Cl. .............................. 378/4; 378/15; 378/901
(58) Field of Search ........................... 378/4, 8, 15, 19, 378/901; 382/128, 131

(56) References Cited

U.S. PATENT DOCUMENTS

| | | | |
|---|---|---|---|
| 5,999,587 A | * 12/1999 | Ning et al. | 378/4 |
| 6,263,040 B1 | 7/2001 | Hsieh | 378/15 |
| 6,332,013 B1 | 12/2001 | Hsieh | 378/15 |
| 6,415,012 B1 | 7/2002 | Taguchi et al. | 378/15 |
| 6,477,221 B1 | * 11/2002 | Ning | 378/4 |
| 6,504,892 B1 | * 1/2003 | Ning | 378/4 |
| 6,678,346 B2 | * 1/2004 | Hsieh | 378/4 |

OTHER PUBLICATIONS

Harrison H. Barrett and William Swindell, Department of Radiology and Optical Sciences Center University of Arizona, *Radiological Imaging, The Theory of Image Formation, Detection, and Processing*, vol. 2, Academic Press, New York, London, Paris, San Diego, San Francisco, Sao Paulo, Sydney, Tokyo, Toronto, 1981, pp. 391–392.

Dennis L. Parker, "Optical short scan convolution reconstruction for fanbeam CT," Med. Phys. 9(2), Mar./Apr. 1982, pp. 254–257.

Marc Kachelriess, et al., "Advanced single–slice rebinning for tilted spiral cone–beam CT," Med. Phys. 28(6), Jun. 2001, pp. 1033–1041.

L.A. Feldkamp, L.C. Davis, and J.W. Kress, "Practical cone–beam algorithm," J. Opt. Soc. Am. A/vol. 1. No. 6, Jun. 1984, pp. 612–919.

Henrik Turbell and Per–Erik Danielsson, "Fast Feldkamp Reconstruction," Image Processing Lab., Dept. of Electrical Engineering, Linkoping University, Sweden.

* cited by examiner

*Primary Examiner*—Edward J. Glick
*Assistant Examiner*—Courtney Thomas
(74) *Attorney, Agent, or Firm*—Oblon, Spivak, McClelland, Maier & Neustadt, P.C.

(57) ABSTRACT

An X-ray computed tomography apparatus includes a helical scanning device configured to collect projection data while at least one of a gantry and a couch moves along a body axial direction of an object on the couch when at least one of the gantry and the couch is tilted, the helical scanning device including an X-ray source configured to generate X-rays, and a detector disposed opposite the X-ray source and having detector elements arranged in a plurality of rows along the body axial direction, and a reconstructing device configured to reconstruct an image based on the projection data using cone-beam Feldkamp reconstruction.

18 Claims, 9 Drawing Sheets

Z-AXIAL
DIRECTION
SLICE DIRECTION

TILTED GANTRY HELICAL CONE-BEAM FELDKAMP RECONSTRUCTION FOR MULTISLICE CT

BACKGROUND OF THE INVENTION

1. Field of the Invention

The present invention relates generally to an X-ray computed tomography (CT) apparatus. More particularly, in a multi-slice X-ray CT apparatus that uses a plurality of rows of detectors for detecting an X-ray image formed by helical scanning of the surroundings of a subject, this invention relates to a technique for achieving data interpolation and image reconstruction based on data obtained from helical scanning of the subject while the patient couch or gantry is tilted. Specifically, the invention relates to the reconstruction of CT scans for a tilted gantry or tilted couch implementing a 3-D Feldkamp cone-beam based reconstruction algorithm.

2. Discussion of the Background

There have previously been proposed X-ray CT devices using a helical scanning system. As illustrated in FIG. 5, the X-ray CT apparatus based on helical scanning collects tomographic image data of a subject to be examined by moving a patient couch in a body axial direction of the subject 12, along the Z axis, in synchronism with a continuous rotation of both an X-ray beam generation source (focus) 13 and a detector 11. Therefore, in the helical scanning system, the X-ray CT apparatus moves the patient couch in a body axial direction of the subject 12 through a center of the rotation of the X-ray focus 13 and the detector 11 while rotating these units. Through this process, the X-ray focus 13 and the detector 11 take a spiral locus around the subject 12 as illustrated in FIG. 4.

There are two types of helical scanning devices: single slice and multi-slice. A single slice CT device has an X-ray beam generation source for irradiating fan shaped X-ray beams (hereafter referred to as fan beams) and a detector having M channels (for example 1,000 channels) arrayed in a fan shape or in a linear shape in one row. This single slice CT device has an X-ray beam generation source and a detector that rotate around the subject. M data is collected in one rotation. Data collection for a single time period is referred to as "one view."

The second type of helical scanning device, a multi-slice CT scanning device, has an X-ray beam generation source for irradiating conical X-ray beams (hereafter referred to as cone-beams), and a two dimensional detector having detectors arrayed in a body axis (Z axis) direction in a plurality of rows, each detector having an arcuate array of M channel detectors (M channels times N rows). The multi-slice CT device rotates the X-ray focus and the detector around the subject, and collects M×N data in one rotation. Accordingly, as compared with the single-slice CT apparatus, it is possible to scan over a wide range with higher precision and higher speed.

Image reconstruction processing in a helical scanning system includes several steps, as illustrated in FIGS. 6A and 6B. First, as shown in FIG. 6A, projection data collected by the detector at each view of the helical scanning is collected for all angles. The projection data is corrected by taking into consideration the sensitivity of the detector, the X-ray intensity, and various other physical factors. The data after correction is referred to as raw data.

The raw data is then interpolated to generate interpolated data on a desired slice surface. This type of interpolation is known as helical interpolation. The interpolation may be performed using adjacent interpolation, as disclosed for example in Japanese Laid-open Publication Hei 4-224736. Filter interpolation for the addition of weighted multi-point data may also be performed using techniques similar to those described in Japanese Laid-open Publication Hei 9-234195. Other interpolation methods, such as opposite beam interpolation and the like may also be used.

The interpolated data for the respective angles are then subjected to a convolution calculation, as illustrated in FIG. 6B. The convolution calculation uses a filter function selected based on the properties of the X-ray CT device.

The convolved data is then added to all the pixels arrayed along the path of an X-ray beam at the time of data collection. This process is known as backprojection. The backprojection is repeated for all of the convolved data at angles according to the beam shape, thereby leaving only the original signal.

In order to reconstruct the original signal, fan beam reconstruction has often been used, especially in the case of a tilted gantry or tilted patient couch. In order to prevent unnecessary patient exposure to X-rays during CT scans, it is useful to tilt the gantry about the patient or to tilt the couch during scanning. Without compensation for artifacts introduced during the tilting of the gantry or couch, the quality of reconstructed images is poor. In the past, fan beam reconstruction of tilted gantry CT scans has been performed in order to correct for artifacts introduced during the tilt.

However, fan beam reconstruction is an approximation useful for small cone angles associated with multi-slice systems of four or less slices. For larger multi-slice systems, such as those having eight or sixteen slices, the fan beam approximation becomes less and less accurate. As a result, unacceptable artifacts such as loss of resolution and inaccurate structure reconstruction occur.

In previous methods using the ASSR method (described, for example, in M. Kachelriess, T. Fuchs, S. Schaller, and W. A. Kalendar, "Advanced Single-Slice Rebinning for Tilted Spiral Cone-Beam CT," *Med. Phys.* 28(6), pp. 1033–1041 (June 2001), the contents of which are herein incorporated by reference), it was not possible to compensate for arbitrary pitch values. Additionally, for incorporating the tilt of the gantry, ASSR requires complete reformulation of the reconstruction problem.

SUMMARY OF THE INVENTION

Accordingly, in light of the above-described difficulties, an object of this invention is to provide a method, system, and computer program product for 3D Feldkamp cone-beam reconstruction using a tilted gantry helical reconstruction algorithm (THFK) for use in the cone-beam helical CT case.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
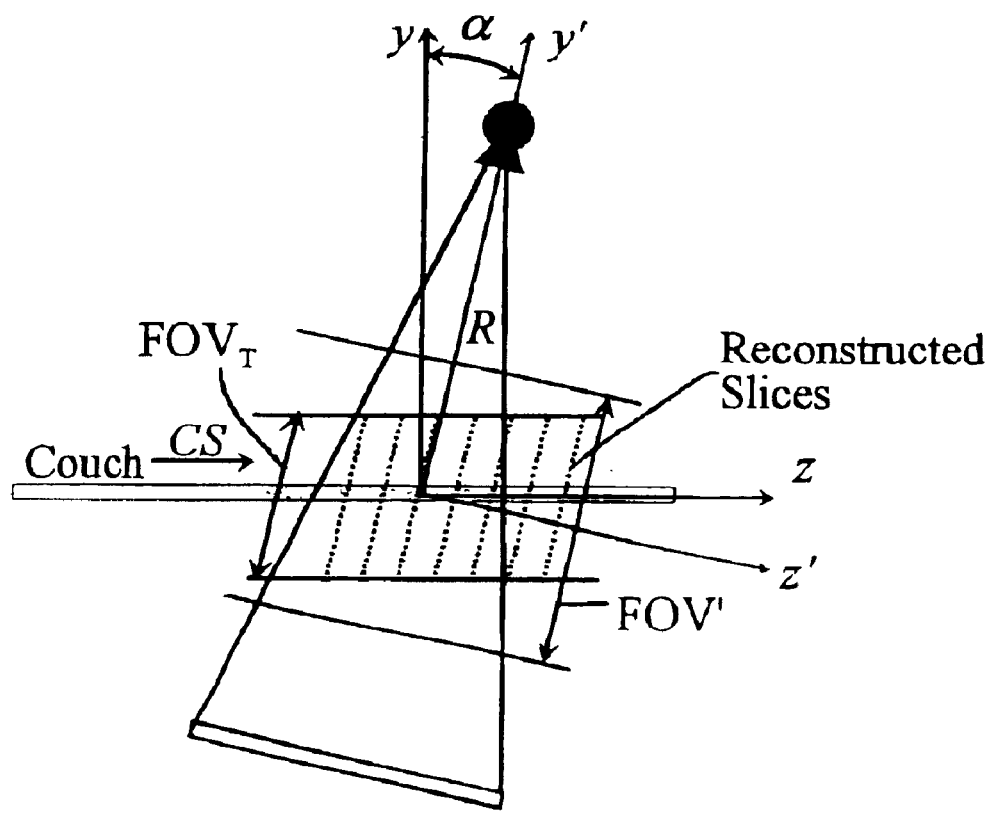
FIG. 1 illustrates tilted helical geometry and slice reconstruction.

Referring now to the drawings, wherein like reference numerals designate identical or corresponding parts throughout the several views, FIG. 1 illustrates the geometry of tilted gantry or tilted couch helical reconstruction using slices. The plane of gantry rotation is located in the y'x plane, which is titled by an angle α as shown. The patient couch moves with a constant velocity of CS mm/rotation along the z axis, and FOV' is the maximum field of view with respect to the rotation axis z'. $FOV_T$ is the tilted field of view, and $FOV_T$ is always smaller than FOV'. The plane of the reconstructed slices is parallel to the plane of rotation (y'x plane), but the FOV' centers of the slices are located on the z axis, not on the gantry rotation axis z'. As a result, the isocenter for a given reconstructed slice moves in the direction y' as the gantry rotates.

Figure 2:
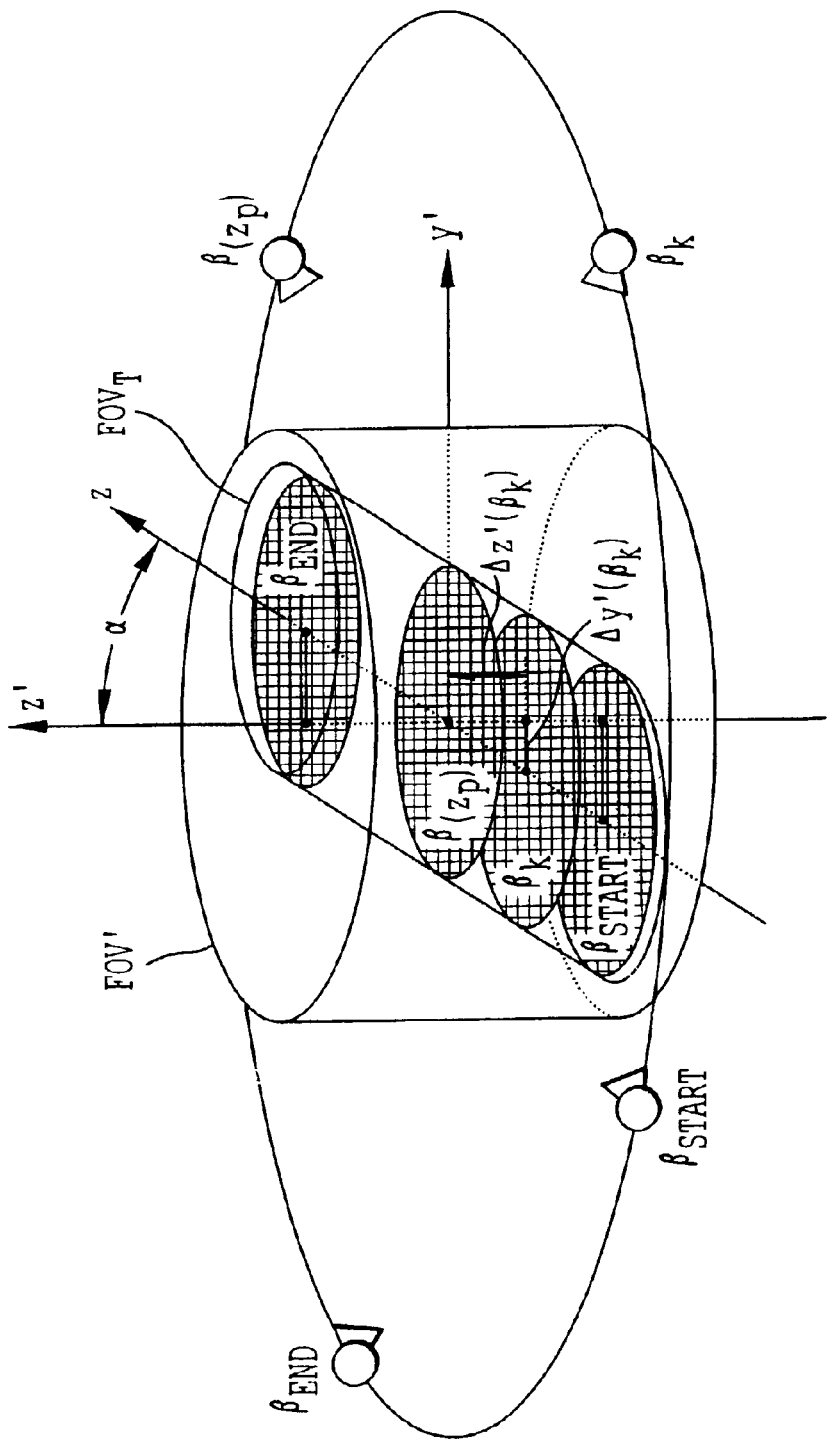
FIG. 2 illustrates the motion of a field of view (FOV) of interest.

This movement of the isocenter in the direction y' is illustrated in FIG. 2, which depicts the motion of an FOV of interest as a function of the view angle β. The slice position is located in absolute coordinates at $z=z_p$, where $z=0$ corresponds to the first view in the data set. The angle of view corresponding to $z_p$ is defined as:

$$\beta(z_p) = 360 \cdot \left( int\left[ \frac{k_{zp}}{N_{\beta rot}} \right] + \frac{TP(k_{zp})}{N_{\beta rot}} \right) + 120° \quad (1)$$

$$k_{zp} = \frac{360 \cdot z_p}{CS \cdot \Delta \beta} \quad (2)$$

and TP is the tube position, which is an integer ranging from zero to $N_{\beta rot}-1$, and is encoded in each projection view.

As with non-tilted Feldkamp (techniques of which may be found in L. A. Feldkamp, L. C. Davis, and J. W. Kress, "Practical Cone-Beam Algorithm," *Journal Optical Society of America*, Vol. 1, pp612–619 (1984), the contents of which are incorporated herein by reference) the view reconstruction range $\beta_{RR}$ is centered at $\beta(z_p)$, with as starting position defined as:

$$\beta_{start}(z_p) = \beta(z_p) - \frac{\beta_{RR}}{2} \quad (3)$$

and an ending position defined as:

$$\beta_{end}(z_p) = \beta(z_p) + \frac{\beta_{RR}}{2} \quad (4)$$

where $\beta_{RR}$ is the angular backprojection range and $\beta_{start} \leq \beta_k \leq \beta_{end}$. The first z position, $z_{pmin}$, that may be reconstructed corresponds to the view $\beta_{1st\_view}+\beta_{RR}/2$, or $$z_{pmin} = \frac{\beta_{RR} \cdot CS}{720} \quad (5)$$

Once the backprojection view range is defined, the projection view data for the range is weighted (using techniques such as those described in Dennis L. Parker, "Optimal Short Scan Convolution Reconstruction for Fanbeam CT," *Med. Phys.* 9(2), March/April 1982, the contents of which are herein incorporated by reference), and convolved (using techniques analogous to those described in H. H. Barrett and W. Swindell, *Radiological Imaging: Theory of Image Formation, Detection, and Processing*, Vol. 2, New York: Academic Press, pp391–392 (1981), the contents of which is herein incorporated by reference) as desired prior to backprojection.

In the tilted case, the relative y-position Δy' and z-position Δz' of the slice of interest are a function of β, and are given as follows:

$$\Delta y'(\beta_k) = \frac{[\beta_k - \beta(z_p)] \cdot CS \cdot \sin\alpha}{360} \quad (6)$$

$$\Delta z'(\beta_k) = \frac{[\beta_k - \beta(z_p)] \cdot CS \cdot \cos\alpha}{360} \quad (7)$$

Because of the tilt, $FOV_T<FOV'$, and the maximum $FOV_T$ is given by $$FOV_{T\,max} = FOV' - \Delta y'(\beta_{RR/2}) \quad (8)$$

Figure 3A:
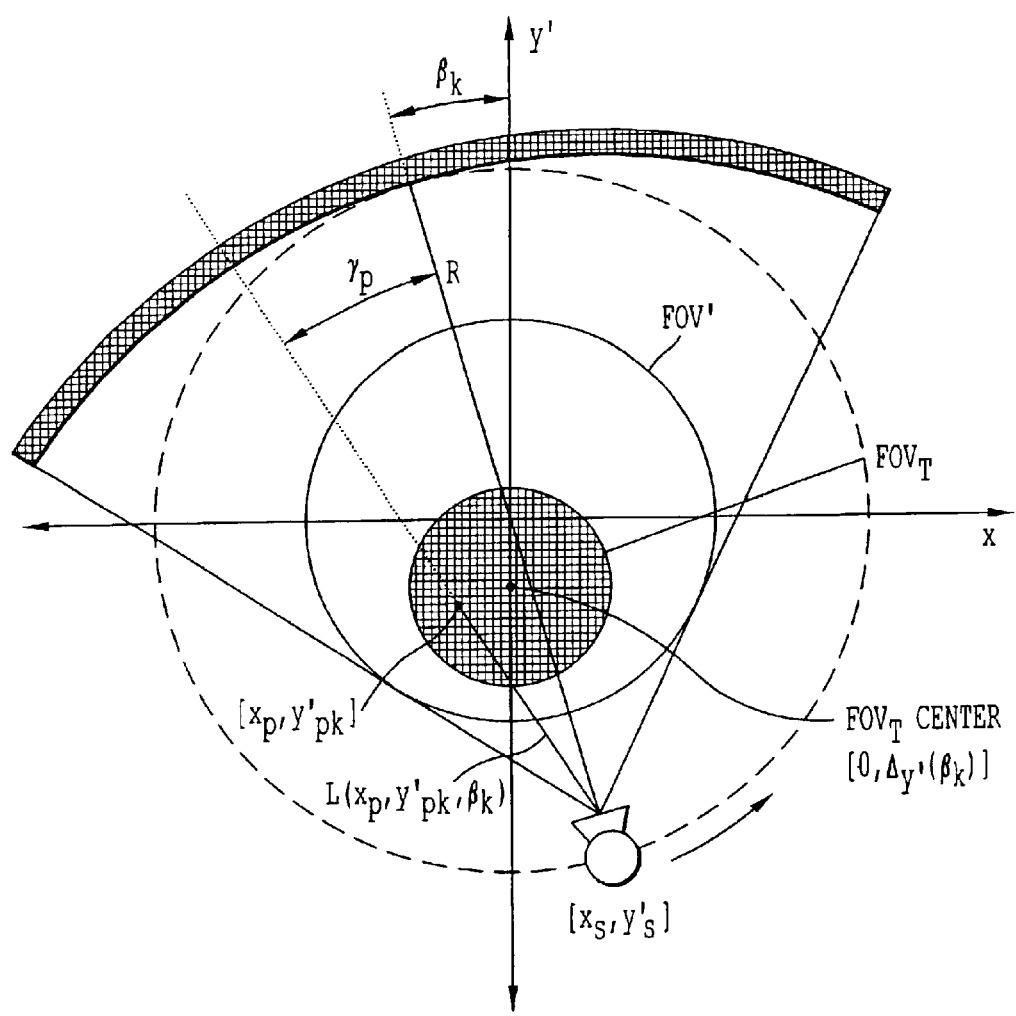
FIG. 3 depicts the geometry of backprojection.
Figure 3B:
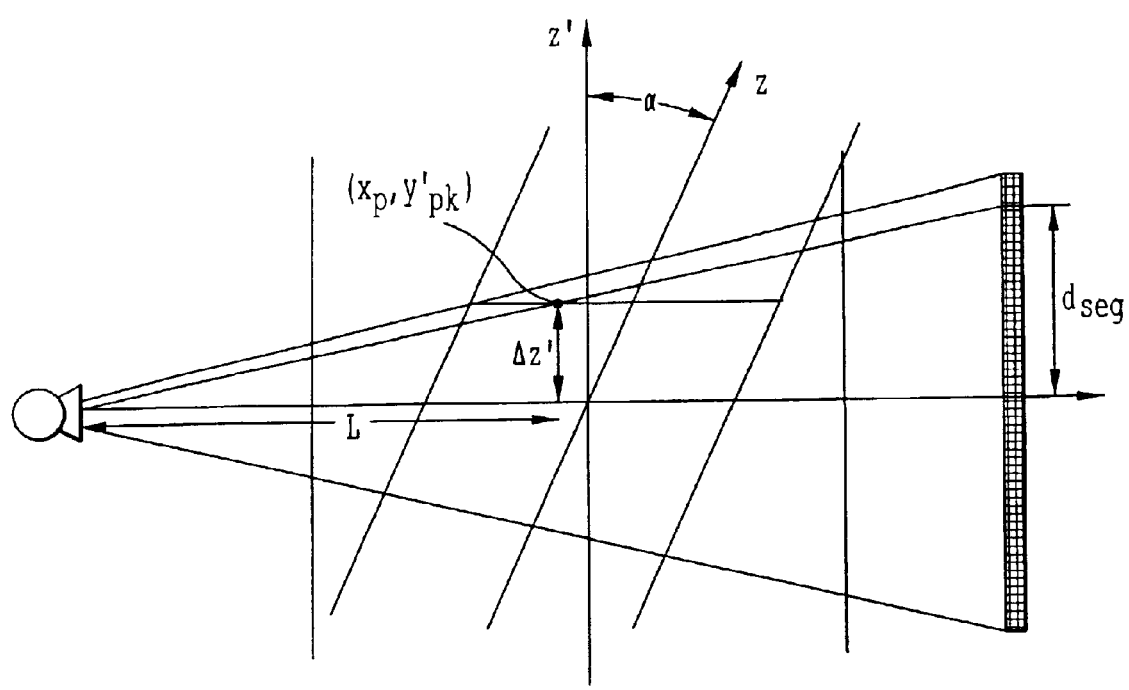

As shown in FIG. 3, the segment position of the projected ray for view $\beta_k$ at point $(x_p, y'_p, z_p)$ is $$d_{seg}(x_p, y'_{pk}, \beta_k) = \frac{\Delta z'(\beta_k) \cdot R}{L(x_p, y'_{pk}, \beta_k)} \quad (9)$$

where $$L(x_p, y'_{pk}, \beta_k) = \sqrt{(R\sin\beta_k+x_p)^2 + (R\cos\beta_k-y'_{pk})^2} \quad (10)$$

and $$y'_{pk} = y'_p + \Delta y'(\beta_k) \quad (11)$$

The segment number is $$j_{seg}(x_p, y'_{pk}, \beta_k) = \frac{d_{seg}(x_p, y'_{pk}, \beta_k)}{w} + j_o \quad (12)$$

where $$j_o = \frac{N_{seg}}{2} \quad (13)$$

The channel position is given by $$\gamma_p(x_p, y'_p, \beta_k) = \tan^{-1}\left[ \frac{x_p\cos\beta_k + y'_{pk}\sin\beta_k}{R + x_p\sin\beta_k - y'_{pk}\cos\beta_k} \right] \quad (14)$$

with channel number $$i_{ch}(x_p, y'_{pk}, \beta_k) = \frac{\gamma_p(x_p, y'_{pk}, \beta_k)}{\Delta\gamma} + i_o + CR_{Offset} \quad (15)$$

where $$i_o = \frac{N_{ch}}{2} \quad (16)$$

and $$\Delta\gamma = \frac{2\gamma_{max}}{N_{ch}} \quad (17)$$

The reconstructed tilted field of view $FOV_T$ is the default FOV divided by the zoom factor $Z_s$:

$$FOV_T = \frac{FOV}{Z_F} \quad (18)$$

where $Z_s=1.0$ for the default FOV case with no zooming. The reconstruction x and y increments $x_{inc}$ and $y_{inc}$ are:

$$x_{inc} = \frac{FOV_T}{N_i} \quad (19)$$

$$y_{inc} = \frac{FOV_T}{N_j} \quad (20)$$

The parameters $X_o$ and $Y_o$ define the center of the reconstruction. The starting x and y positions for the back-projection are:

$$x_{start} = X_o - \frac{FOV_T}{2} \quad (21)$$

$$y_{start} = Y_o - \frac{FOV_T}{2} \quad (22)$$

Figure 4:
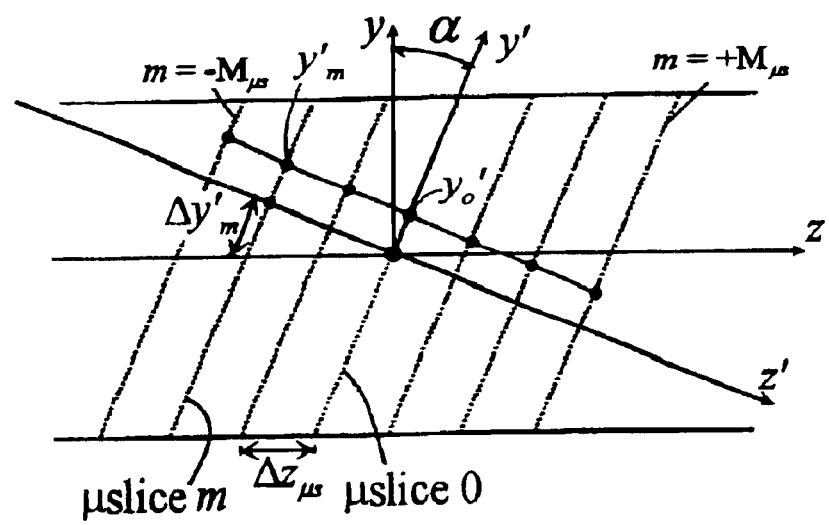
FIG. 4 illustrates microslice stacking.
Figure 5:
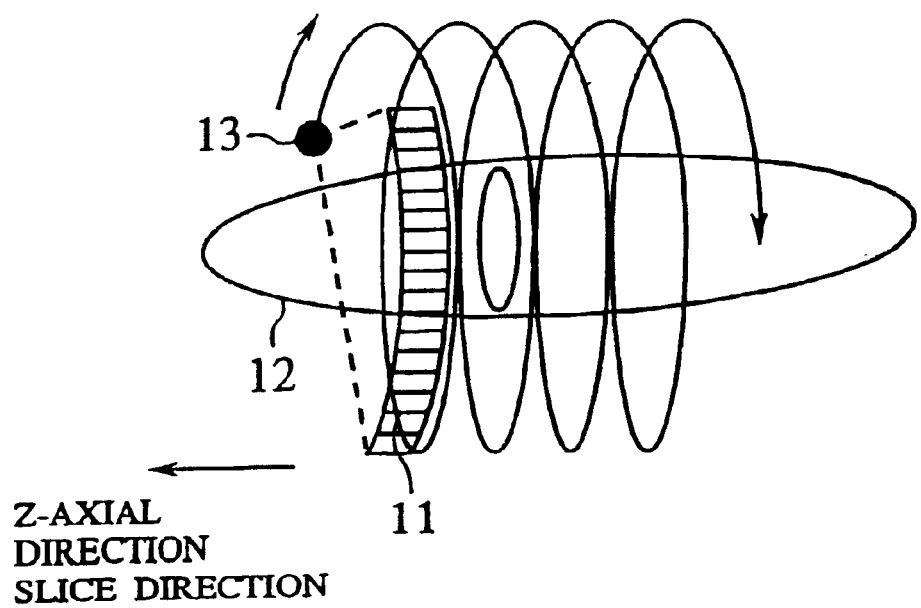
FIG. 5 illustrates a helical CT scanning system.
Figure 6A:
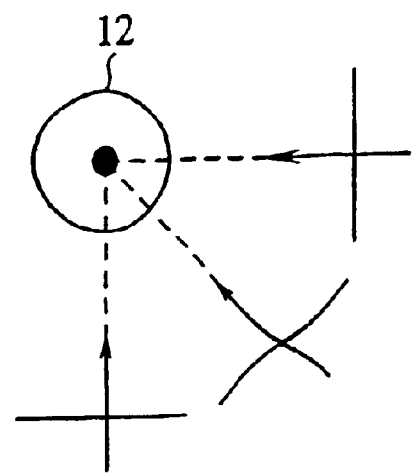
FIGS. 6A and 6B illustrate image reconstruction processing of helical CT data.
Figure 6B:
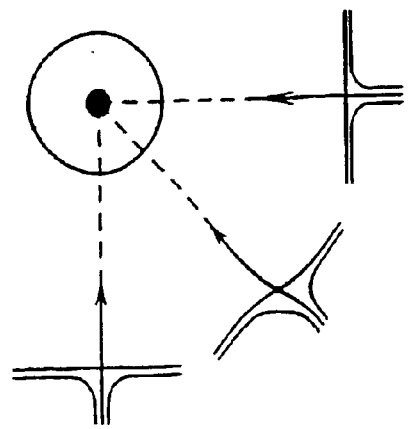
Figure 7:
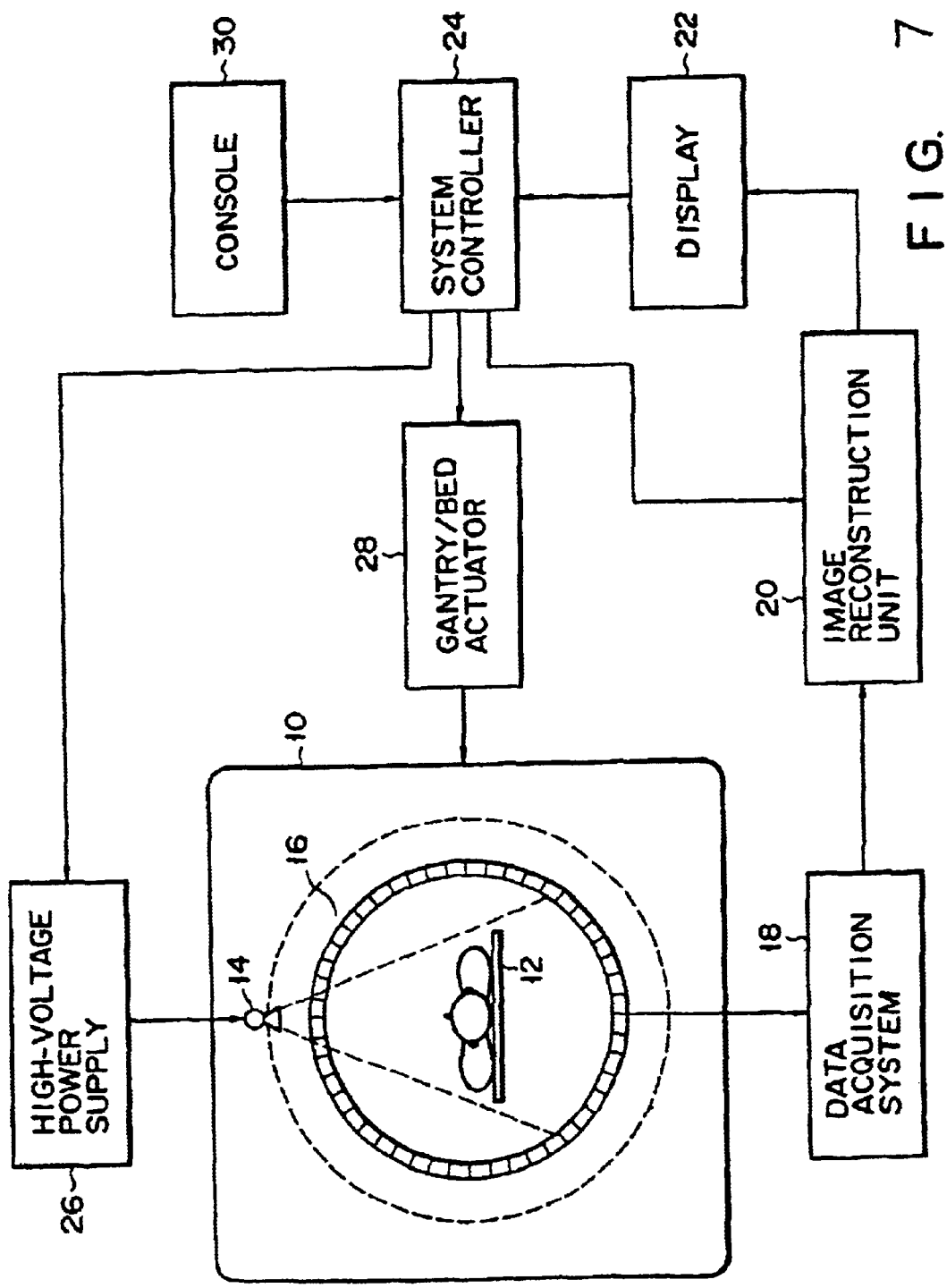
FIG. 7 represents a non-limiting embodiment of an X-ray CT apparatus according to the present invention.
Figure 8:
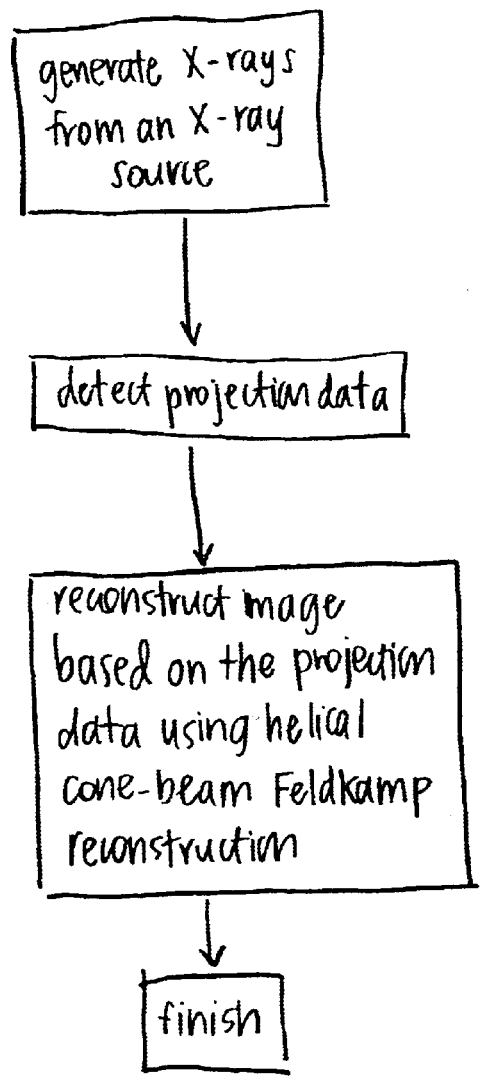
FIG. 8 represents a non-limiting embodiment of a method for an X-ray CT according to the present invention.

Micro-slice stacking is implemented along the z'-axis, as shown in FIG. 4. The center micro-slice is located at k=0, and for pixel located at position x, $y_o$, the stacking is along the green line. Since the micro-slices are centered on the z-axis, this implementation assumes there is an odd number of micro-slices.

According to the present invention, the use of the Feldkamp equations yields an improved CT scan image with fewer artifacts.

Computer and System

The source of image data may be any appropriate image acquisition device such as an X-ray machine, CT apparatus, and MRI apparatus. Further, the acquired data may be digitized if not already in digital form. Alternatively, the source of image data being obtained and processed may be a memory storing data produced by an image acquisition device, and the memory may be local or remote, in which case a data communication network, such as PACS (Picture Archiving Computer System), can be used to access the image data for processing according to the present invention.

This invention conveniently may be implemented using a conventional general purpose computer or micro-processor programmed according to the teachings of the present invention, as will be apparent to those skilled in the computer art. Appropriate software may readily be prepared by programmers of ordinary skill based on the teachings of the present disclosure, as will be apparent to those skilled in the software art.

A computer implements the method of the present invention, wherein the computer housing houses a motherboard which contains a CPU, memory (e.g., DRAM, ROM, EPROM, EEPROM, SRAM, SDRAM, and Flash RAM), and other optical special purpose logic devices (e.g., ASICS) or configurable logic devices (e.g., GAL and reprogrammable FPGA). The computer may also include plural input devices, (e.g., keyboard and mouse), and a display card for controlling a monitor. Additionally, the computer may include a floppy disk drive; other removable media devices (e.g. compact disc, tape, and removable magneto-optical media); and a hard disk or other fixed high density media drives, connected using an appropriate device bus (e.g., a SCSI bus, an Enhanced IDE bus, or an Ultra DMA bus). The computer may also include a compact disc reader, a compact disc reader/writer unit, or a compact disc jukebox, which may be connected to the same device bus or to another device bus.

As stated above, the system includes at least one computer readable medium. Examples of computer readable media are compact discs, hard disks, floppy disks, tape, magneto-optical disks, PROMS (e.g., EPROM, EEPROM, Flash EPROM), DRAM, SRAM, SDRAM, etc. Stored on any one or on a combination of computer readable media, the present invention includes software for controlling both the hardware of the computer and for enabling the computer to interact with a human user. Such software may include, but is not limited to, device drivers, operating systems and user applications, such as development tools. Computer program products of the present invention include any computer readable medium which stores computer program instructions (e.g. computer code devices) which when executed by a computer causes the computer to perform the method of the present invention. The computer code devices of the present invention can be any interpreted or executable code mechanism, including but not limited to, scripts, interpreters, dynamic link libraries, Java classes, and complete executable programs. Moreover, parts of the processing of the present invention may be distributed for better performance, reliability, and/or cost. For example, an outline or image may be selected on a first computer and sent to a second computer for remote diagnosis.

The invention may also be implemented by the preparation of application specific integrated circuits or by interconnecting an appropriate network of conventional component circuits, as will be readily apparent to those skilled in the art.

Numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An X-ray computed tomography apparatus, comprising:
    a helical scanning device configured to collect projection data while at least one of a gantry and a couch moves along a body axial direction of an object on the couch when at least one of the gantry and the couch is tilted, thereby forming a tilted rotation axis, the helical scanning device including,
        an X-ray source configured to generate X-rays and to rotate around the object, and
        a detector having detector elements arranged in a plurality of rows along the body axial direction opposite the X-ray source; and
    a reconstructing device configured to reconstruct an image based on the projection data using helical cone-beam Feldkamp reconstruction.

2. The X-ray computed tomography apparatus according to claim 1, wherein the reconstructing device comprises a mechanism configured to reconstruct the image using the cone-beam Feldkamp reconstruction according to a tilt angle when the at least one of the gantry and the couch is tilted.

3. The X-ray computed tomography apparatus according to claim 1, wherein the reconstructing device comprises a mechanism configured to reconstruct the image of a reconstructing plane according to a tilt angle when the at least one of the gantry and the couch is tilted.

4. The X-ray computed tomography apparatus according to claim 1, wherein the reconstructing device comprises a mechanism configured to shift the image based on a tilt angle when the at least one of the gantry and the couch is tilted.

5. The X-ray computed tomography apparatus according to claim 1, wherein the reconstructing device comprises a mechanism configured to shift the image based on a tilt angle when data from the projection data is backprojected.

6. The X-ray computed tomography apparatus according to claim 1, wherein the reconstructing device comprises a mechanism configured to shift the image based on a tilt angle and based on a projection angle of the projection data.

7. The X-ray computed tomography apparatus according to claim 1, wherein the reconstructing device comprises a filtering mechanism configured to acquire at least one image of predetermined slice thickness by filtering the at least one image along the tilted rotation axis.

8. The X-ray computed tomography apparatus according to claim 1, wherein the reconstructing device comprises a filtering mechanism configured to acquire an image of predetermined slice thickness by filtering the projection data along the tilted rotation axis while the projection data is backprojected.

9. An X-ray computed tomography apparatus, comprising:
a helical scanning device configured to collect projection data while at least one of a gantry and a couch moves along a body axial direction of an object on the couch when at least one of the gantry and the couch is tilted, the helical scanning device including,
an X-ray source configured to generate X-rays, and
a detector disposed opposite the X-ray source and having detector elements arranged in a plurality of rows along the body axial direction; and
means for reconstructing an image based on the projection data using helical cone-beam Feldkamp reconstruction.

10. A method for X-ray computed tomography, comprising:
helically scanning an object with X-rays to collect projection data while at least one of a gantry and a couch moves along a body axial direction of an object on the couch when at least one of the gantry and the couch is tilted, thereby forming a tilted rotation axis, the helically scanning including,
generating X-rays from an X-ray source, and
detecting projection data using a detector disposed opposite the X-ray source and having detector elements arranged in a plurality of rows along the body axial direction; and
reconstructing an image based on the projection data using helical cone-beam Feldkamp reconstruction.

11. The method according to claim 10, wherein the reconstructing step comprises:
reconstructing the image using the cone-beam Feldkamp reconstruction according to a tilt angle when the at least one of the gantry and the couch is tilted.

12. The method according to claim 10, wherein the reconstructing step comprises:
reconstructing the image of a reconstructing plane according to a tilt angle when the at least one of the gantry and the couch is tilted.

13. The method according to claim 10, wherein the reconstructing step comprises:
shifting the image based on a tilt angle when the at least one of the gantry and the couch is tilted.

14. The method according to claim 10, wherein the reconstructing step comprises:
shifting the image based on a tilt angle when the projection data is backprojected.

15. The method according to claim 11, wherein the reconstructing step comprises:
shifting the image based on a tilt angle and based on a projection angle of the projection data.

16. The method according to claim 10, wherein the reconstructing step comprises:
filtering the image along the tilted rotation axis to acquire an image of predetermined slice thickness.

17. The method according to claim 10, wherein the reconstructing step comprises:
filtering the image along the tilted rotation axis while the projection data is backprojected to acquire an image of predetermined slice thickness.

18. A computer program product storing instructions for execution on a computer system, which when executed by the computer system, causes the computer system to perform the method recited in any one of claims 10–17.

* * * * *